United States Patent [19]

Shutske et al.

[11] Patent Number: 5,264,576
[45] Date of Patent: Nov. 23, 1993

[54] PYRAZOLO[4,3-C]PYRIDINES WHICH ARE INTERMEDIATES

[75] Inventors: Gregory M. Shutske, Flemington; Kevin J. Kapples, Little York, both of N.J.; John D. Tomer, IV, Perkasie, Pa.

[73] Assignee: Hoechst-Roussel Pharmaceuticals Incorporated, Somerville, N.J.

[21] Appl. No.: 964,690

[22] Filed: Oct. 22, 1992

[51] Int. Cl.$^5$ .......................................... C07D 471/04
[52] U.S. Cl. ................................................... 546/119
[58] Field of Search ........................................ 546/119

[56] References Cited

U.S. PATENT DOCUMENTS 4,500,525 2/1985 Winters et al. ...................... 514/210

FOREIGN PATENT DOCUMENTS 51-125281 11/1976 Japan .
52-14765 3/1977 Japan .

OTHER PUBLICATIONS

Radinov et al., J. of Molecular Structure, vol. 158, pp. 99–108 (1987).

Primary Examiner—Bernard Dentz
Attorney, Agent, or Firm—Elliott Korsen, Esq.

[57] ABSTRACT

There are disclosed novel pyrazolo[4,3-c]pyridines of the formula

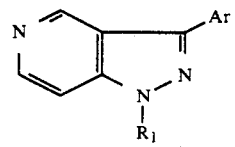

where Ar and $R_1$ are as defined in the specification, which are useful as serotonin reuptake inhibitors and as such may be useful for the treatment of depression, obsessive-compulsive disorders, stuttering and trichotillomania.

7 Claims, No Drawings

PYRAZOLO[4,3-C]PYRIDINES WHICH ARE INTERMEDIATES

The present invention relates to compounds of the general formula

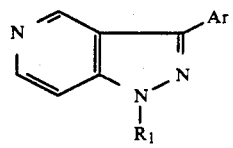

wherein
Ar is

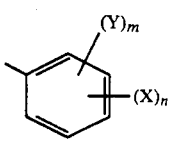

or pyridyl;
$R_1$ is H, —$(CH_2)_pNR_2R_3$,

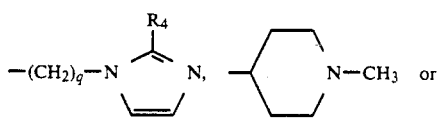

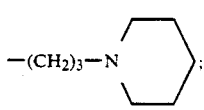

$R_2$ is hydrogen or loweralkyl;
$R_3$ is hydrogen or loweralkyl;
$R_4$ is hydrogen or loweralkyl;
X and Y are independently hydrogen, halogen, trifluoromethyl, nitro, loweralkyl, loweralkoxy or hydroxy;
n is 1, 2 or 3;
m is 1 or 2;
p and q are independently 2, 3 or 4;
or a pharmaceutically acceptable addition salt and/or hydrate thereof, or where applicable, a geometric or optical isomer or racemic mixture thereof.

This invention also relates to a process for making the compounds and to pharmaceutical compositions, and methods of use as serotonin reuptake inhibitors.

The compounds of this invention are useful as serotonin reuptake inhibitors and as such may be useful for the treatment of depression, obsessive-compulsive disorders, stuttering and trichotillomania.

Unless otherwise stated or indicated, the following definitions shall apply throughout the specification and appended claims.

The term lower shall mean the group it is describing contains from 1 to 6 carbon atoms.

The term loweralkyl shall mean a straight or branched alkyl group having from 1 to 6 carbon atoms, e.g., methyl, ethyl, n-propyl, isopropyl, n-butyl, isobutyl, sec-butyl, t-butyl, pentyl and hexyl.

The term halogen shall mean fluorine, chlorine, bromine or iodine.

Throughout the specification and amended claims, a given chemical formula or name shall encompass all stereo and optical isomers where such isomers exist.

Additionally, a given chemical formula or name shall encompass pharmaceutically acceptable addition salts thereof and solvates thereof, such as hydrates.

In a preferred embodiment of this invention are compounds of the formula

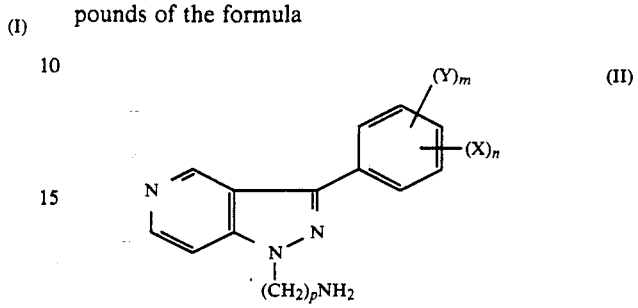

wherein X and Y are independently hydrogen, halogen, trifluoromethyl, loweralkyl, loweralkoxy, nitro or hydroxy;
n is 1, 2 or 3; m is 1 or 2; and p is 2, 3 or 4.

More preferably, X is hydrogen, halogen, loweralkyl, loweralkoxy, trifluoromethyl or nitro and Y is hydrogen, halogen, loweralkyl, loweralkoxy or trifluoromethyl.

Most preferable are compounds wherein X is Cl, Br, F, 4-$CF_3$, 2-$CH_3$, 4-$NO_2$ or 2-$OCH_3$; and
Y is hydrogen or Cl.

In another preferred embodiment of the invention are compounds of the formula

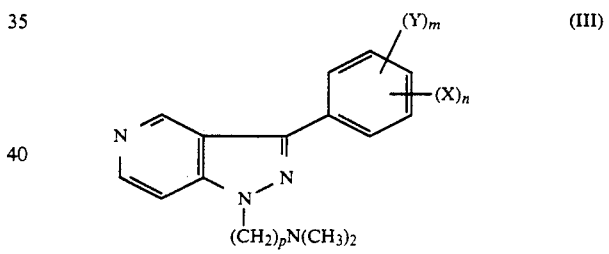

wherein
X and Y are independently hydrogen, halogen or $CF_3$.

More preferably X is halogen or $CF_3$ and Y is hydrogen or halogen.

Most preferable are compounds wherein X is Br or Cl and
Y is hydrogen.

In a third preferred embodiment of the invention are compounds of the formula

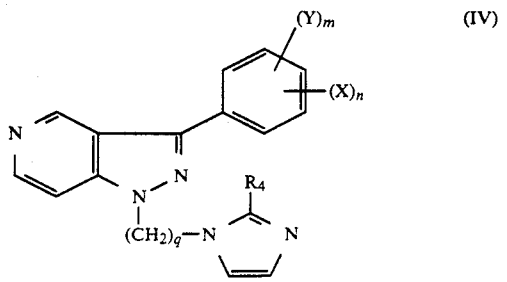

wherein $R_4$ is hydrogen or loweralkyl;

X and Y are independently hydrogen, halogen or trifluoromethyl and q is 2, 3 or 4.

More preferable are compounds of this embodiment wherein $R_4$ is hydrogen or methyl;

X is hydrogen or Cl; Y is hydrogen or Cl; and q is 2.

Also encompassed by this invention are intermediate compounds of the formula (V)

wherein

X and Y are independently hydrogen, halogen, trifluoromethyl, loweralkyl, loweralkoxy, nitro or hydroxy.

More preferably, X is hydrogen or halogen; and Y is hydrogen.

The compounds of this invention are prepared in the following manner. The substituents X, Y, $R_1$, $R_2$, $R_3$, $R_4$, n, m, p and q are as defined above unless indicated otherwise.

PREPARATION

4-Chloropyridine of the formula is reacted with a solution of lithium diisopropylamine and tetrahydrofuran. This reaction typically takes place in a solution of tetrahydrofuran or other suitable solvent at a temperature of about −80° to −40° C. for 2 to 6 hours. After stirring for 2 to 6 hours, a solution of a benzaldehyde or substituted benzaldehyde in tetrahydrofuran is added to give a compound of the formula (VI)

Compound VI in suspension with toluene or other suitable solvents and an oxidizing agent such as manganese (IV) oxide is refluxed for about 1 to 4 hours to give compound VII of the formula (VII)

Compound VII is subsequently treated with hydrazine hydrate and refluxed for 1 to 4 hours to yield a compound VIII of the formula (VIII)

To prepare compound II of the formula (II)

where X, Y, n, m and p are as previously defined, compound VIII in suspension with dimethylformamide or other suitable liquid is reacted with a 2-haloalkylphthalimide and a strong base such as potassium carbonate, sodium hydride or potassium t-butoxide. This mixture is reacted, with stirring, for 1 to 10 hours at 25° to 100° C. to give the phthalimido (alkyl)pyrazole pyridine of the formula (IX)

Compound IX is subsequently warmed in hydrazine hydrate to remove the phthalimide moiety to yield the desired compound.

To prepare compound X of the formula (X)

of the formula, where $R_2$ and $R_3$ are loweralkyl, compound V is suspended in DMF or other suitable liquid and a strong base such as sodium hydride, potassium carbonate or potassium t-butoxide. After stirring for 30 to 120 minutes, a dialkylaminoalkyl chloride is added and the solvent is warmed to about 25° to 100° C. with continued stirring. After 1 to 6 hours, compound X is formed.

To prepare compound XI of the formula

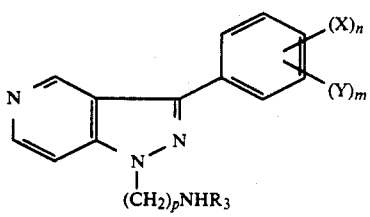 (XI)

where R₃ is loweralkyl, compound II is reacted with methyl trifluoroacetate and a non-nucleophilic base such as triethylamine to yield compound XII of the formula

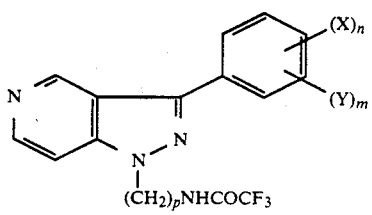 (XII)

Compound XII with potassium t-butoxide or other suitable base is treated with dimethylsulfate or other suitable alkylating agent to yield compound XIII of the formula

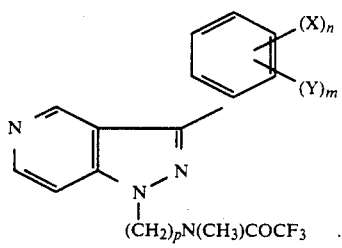 (XIII)

This reaction typically takes place in a polar aprotic solvent such as tetrahydrofuran or N,N-dimethylformamide at a temperature of about 0° to 50° C. for 1 to 4 hours.

Compound XIII is subsequently stirred in a mixture of methanol and saturated potassium carbonate solution to yield the desired compound.

In order to prepare compound IV of the formula

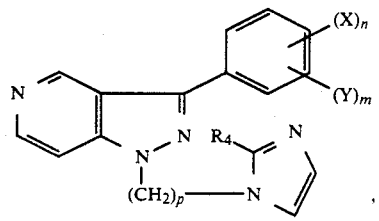

compound V in dimethylformamide or other suitable solvent is reacted with a 1-(2-haloalkyl)imidazole of the formula

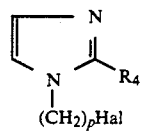 (XIV)

and potassium carbonate. The 1-(2-haloalkyl)imidazole is prepared as described in Foguet Ambros, R., Forne Felop, E., Ortiz Hernandes, J. A., Span. ES 532,874, Oct. 1, 1985. This reaction typically takes place at a temperature of about 50° to 120° C. for 1 to 5 hours.

To prepare compounds where Ar is pyridyl, compound V, where Ar is pyridyl, is reacted as previously described in the preparation of compound II. The starting 3-(4-pyridyl)-1H-pyrazolo[4,3-c]piperidine can be prepared as described for compound VIII using pyridine-4-carboxaldehyde instead of benzaldehyde.

To prepare compounds where R₁ is methyl piperidine, compound XV of the formula

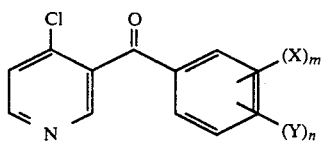 (XV)

is reacted with compound XVI of the formula

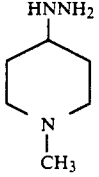 (XVI)

and titanium isopropoxide to yield compound XVII of the formula

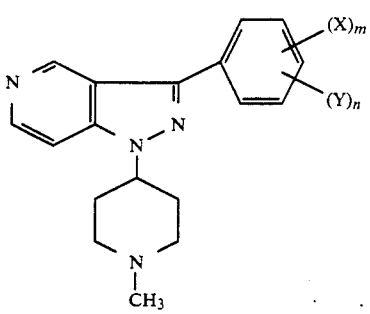 (XVII)

Compound XVI is prepared as described in Ebnother, A., Jucker, E., Lindenmann, A., Rissi, E., Steiner, R, Suess, R., Vogel, A. Helv. Chim. Acta, 42, 533 (1959). This reaction is typically conducted in an inert solvent such as dichloromethane or toluene at a temperature of about 0° to 50° C. for 12 to 72 hours. The hydrazone intermediate formed of the formula $$\text{(XVIII)}$$

is reacted in tetrahydrofuran with potassium t-butoxide at about 0° to 50° C. for 0.5 to 4 hours.

Finally, to prepare compound XIX of the invention of the formula $$\text{(XIX)}$$

compound V is reacted with potassium carbonate or other suitable base and a ω-haloalkyl piperidine to yield compound XIX.

This reaction is typically conducted at a temperature of about 50° to 120° C. for 1 to 5 hours.

The compounds of the present invention may be useful for the treatment of depression and/or obsessive competitive disorder by virtue of their ability to inhibit the reuptake of serotonin.

[$^3$H]-Serotonin Uptake in Rat Whole Brain and Hypothalamic Synaptosomes

Some researchers have suggested that subjects with serotonergic hypofunction comprise a biochemical subgroup of depressed patients. Others claim that altered serotonergic function determines the change associated with obsessive-compulsive disorder.

This activity is determined in an assay which measures [$^3$H]-serotonin uptake in rat whole brain and hypothalamic synaptosomes. The assay described below is used as a biochemical screen for potential antidepressants which block serotonin (5-hydroxytryptamine (5HT)) uptake.

[$^3$H]-5HT transport has been characterized in the central nervous system tissue and found to be saturable, sodium and temperature-dependent, inhibited by ouabain, metabolic inhibitors, tryptamine analogs and tricyclic antidepressants.

Procedure
A. Animals
Male CR Wistar rats (100–125 g)
B. Reagents
1. Krebs-Henseleit Bicarbonate Buffer, pH 7.4 (KHBB):
Prepare a 1 liter batch containing the following salts.

|  | grams/l | mM |
|---|---|---|
| NaCl | 6.92 | 118.4 |
| KCl | 0.35 | 4.7 |
| MgSO$_4$.7H$_2$O | 0.29 | 1.2 |
| KH$_2$PO$_4$ | 0.16 | 2.2 |
| NaHCO$_3$ | 2.10 | 24.9 |
| CaCl$_2$ | 0.14 | 1.3 |

Prior to use add to 200 ml, per assay:

| Dextrose | 2 mg/ml | 11.1 |
|---|---|---|
| Iproniazid phosphate | 0.30 mg/ml | 0.1 |

The batch is aerated for 60 minutes with 95% O$_2$/5% CO$_2$, the pH is checked to insure it is at 7.4±0.1, then add bovine serum albumin (Sigma cat# A-7906) 1 mg/ml.

2. Filtration buffer:
Make a 4 liter batch, containing the following salts:

|  | grams/4 L | mM |
|---|---|---|
| NaCl | 31.68 | 135.5 |
| KCl | 1.40 | 4.7 |
| MgSO$_4$.7H$_2$O | 1.16 | 1.2 |
| HEPES | 9.54 | 10.0 |
| CaCl$_2$ | 0.56 | 1.3 |
| BSA | 4.0 | 1 mg/ml |

Maintain on ice.

3. Sucrose solution: 0.32M sucrose containing 5 mM HEPES and 0.1 mM EDTA; pH to 7.3 using Tris base.
4. A 0.1 mM stock solution of serotonin creatinine SO$_4$ is made up in 0.01N HCl. This is used to dilute the specific activity of the radiolabeled 5HT.
5. 5-[1,2-$^3$H(N)]-Hydroxytryptamine creatinine sulfate (serotonin), specific activity 20–30 Ci/mmol, is used.

The final desired concentration of [$^3$H]-5HT in the assay is 50 mM. The dilution factor is 0.8. The KHBB is made up to contain 62.5 nM of [$^3$H]-5HT.
Add to 100 ml of KHBB.

| A) 56.1 μl of 0.1 mM 5HT = | 56.1 nM |
|---|---|
| B) 0.64 nmol of [$^3$H]-5HT = | 6.4 nM |
|  | 62.5 nM |

6. For most assays, a 0.5 mM stock solution of the test compound is made up initially in either 10 μl of glacial acetic acid, 100 μl DMSO or 10 μl of the recrystallization solvent, to which is added approximately 10 ml of distilled water. Compounds are initially screened in duplicate at 3 concentrations (10$^{-8}$, 10$^{-7}$ and 10$^{-6}$M) made up in water. For those compounds demonstrating activity at <10$^{-7}$ in the initial screen, EC$_{50}$s are determined from 7 concentrations: 10$^{-9}$ through 10$^{-6}$. Higher or lower concentration ranges may be used depending on the potency of the compound. To ensure consistency, the standard chlomipramine is run with each assay.

C. Tissue Preparation
The Percoll method for preparing synaptosomes has been modified from Nagy, A., Delgado-Escueta, A.V.J. Neurochem. 43, 1114 (1984) and Dunkley, P. R., Jarvie, R. E., Heath, J. W., Kidd, G. J., Rostas, J.A.P. Brain Research 372, 115 (1986). Male Wistar rats are decapitated and the brain rapidly removed. Whole brain (minus cerebellum) is weighed and homogenized in 15 volumes of ice cold Sucrose solution using a Potter-Elvejhem homogenizer. The following procedures are performed on ice. Homogenization should be done with 4-5 up and down strokes at medium speeds (setting 4.5 to 5) to minimize synaptosome lysis. The homogenate is centrifuged at 1000 g (3000 rpm, Sorvall SS-34 rotor) for 10 minutes at 0°-4° C. The supernatant is removed and approximately 10 ml per tube is carefully layered onto a discontinuous Percoll (Sigma cat# P-1644) gradient: 21% Percoll in Sucrose solution at the bottom (15 ml per tube) and 10% Percoll in the middle (10 ml; colored with a few drops of phenol red for visibility). The Percoll gradient tubes are carefully placed into a Beckman SW-28 swinging bucket rotor and spun in a Beckman XL90 ultracentrifuge using the following program: speed, 11,000 rpm (15,000 g) for 30 minutes at 4° C.; slow acceleration and deceleration (acceleration setting 9; deceleration setting 3). Tubes are carefully removed, and the top layer and the top part of the middle (red) layer are discarded using a pasteur pipette. The synaptosomes are located in the white fluffy band at the interface between the 10% and 21% Percoll layers. This is carefully removed, placed in a centrifuge tube, diluted with KHBB and spun at 21,000 g (13,000 rpm, Sorvall SS-34 rotor). The pellet (synaptosomes) is resuspended in KHBB (10 vol per gram original brain wet weight; 1 brain minus cerebellum weights approximately 1.2 g; 2.5 brains are needed per typical assay).

D. Assay

| | |
|---|---|
| 800 μl | KHBB with [³H]-5HT |
| 20 μl | Vehicle or appropriate drug |
| 200 μl | Tissue suspension concentration |

200 μl of the tissue suspension are added to each of 24 tubes (at a time) containing the 20 μl of vehicle or drug on ice. Three minutes later, 800 μl of KHBB containing [³H]-5HT are added, and the tubes are vortexed. The rack containing the 24 tubes is moved from the ice bath to a water bath set at 37° C. The tubes are incubated for 5 minutes under 95% $O_2$/5% $CO_2$. Uptake is terminated by filtration through GF/B filter strips using a Brandel cell harvester (filter strips are presoaked in ice cold filtration buffer). Tubes are washed once with 5 ml of ice cold filtration buffer. Filter disks are placed in scintillation vials to which are added 10 ml of scintillation fluid (EcoScint). Filters are allowed to sit overnight before being counted.

For each assay, 3 tubes each are incubated with 20 μl of vehicle at both 37° C. and 0° C. Active uptake is the difference between cpm taken up at 37° C. and 0° C. Percent inhibition at each concentration is the mean of two determinants. $IC_{50}$ values are derived from log probit analysis using #46 Litchfield and Wilcoxon I: confidence limits of $IC_{50}$ Pharmacologic Calculation System-version 4.0.

| Compound | 5-HT Uptake $IC_{50}$ (μM) |
|---|---|
| Chlomipramine (ref.) | 0.018 |
| Fluoxetine (ref.) | 0.048 |
| 1-(2-aminoethyl)-3-(2-bromophenyl)-1H-pyrazolo[4,3-c]pyridine dihydrochloride | 1.53 |
| 1-(2-aminoethyl)-3-(2-methylphenyl)-1H-pyrazolo[4,3-c]pyridine | 0.87 |
| 1-(2-aminoethyl)-3-(4-bromophenyl)-1H-pyrazolo[4,3-c]pyridine | 0.94 |
| 1-(3-aminopropyl)-3-(4-chlorophenyl)-1H-pyrazolo[4,3-c]pyridine dimaleate | 0.77 |
| 1-(2-aminoethyl)-3-(4-trifluoromethylphenyl)-1H-pyrazolo[4,3-c]pyridine maleate | 1.24 |
| 1-(2-aminoethyl)-3-(2,3-dichlorophenyl)-1H-pyrazolo[4,3-c]pyridine fumarate | 0.21 |
| 1-(3-aminopropyl)-3-(2,3-dichlorophenyl)-1H-pyrazolo[4,3-c]pyridine fumarate | 0.41 |
| 1-(2-aminoethyl)-3-(2,4-dichlorophenyl)-1H-pyrazolo[4,3-c]pyridine fumarate | 0.058 |
| 1-(4-aminobutyl)-3-(2,4-dichlorophenyl)-1H-pyrazolo[4,3-c]pyridine dimaleate | 0.095 |
| 1-(2-aminoethyl)-3-(3,4-dichlorophenyl)-1H-pyrazolo[4,3-c]pyridine maleate | 0.21 |
| 1-(3-aminopropyl)-3-(3,4-dichlorophenyl)-1H-pyrazolo[4,3-c]pyridine maleate | 0.24 |
| 1-(2-aminoethyl)-3-(2,3,4-trichlorophenyl)-1H-pyrazolo[4,3-c]pyridine fumarate | 0.049 |
| 1-(3-aminopropyl)-3-(2,3,4-trichlorophenyl)-1H-pyrazolo[4,3-c]pyridine fumarate | 0.023 |

Antidepressant relief is achieved when the compounds of the present invention are administered to a subject requiring such treatment as an effective oral, parenteral, or intravenous dose of from 1 to 100 mg/kg of body weight per day. It is to be understood, however, that for any particular subject, specific dosage regiments should be adjusted according to the individual need and the professional judgment of the person administering or supervising the administration of the aforesaid compound. It is to be further understood that the dosages set forth herein are exemplary only and they do not, to any extent, limit the scope or practice of the invention.

Effective quantities of the compounds of the present invention may be administered to a subject by any one of various methods, for example, orally as in capsules or tablets, parenterally in the form of sterile solutions or suspensions, and in some cases intravenously in the form of sterile solutions.

The compounds of the present invention, while effective themselves, may be formulated and administered in the form of their pharmaceutically acceptable acid addition salts for purposes of stability, convenience of crystallization, increased solubility and the like.

Preferred pharmaceutically acceptable addition salts include salts of inorganic acids such as hydrochloride, hydrobromic, sulfuric, nitric, phosphoric and perchloric acids; as well as salts of organic acids such as tartaric, citric, acetic, succinic, maleic, fumaric, and oxalic acids.

The active compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of compound present in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; and excipient such as starch or lactose, a disintegrating agent such as alginic acid, Primogel ™, corn starch and the like; a lubricant such as magnesium stearate or Sterotex ®; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components; a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of the compounds of this invention include:
3-(4-chlorophenyl)-1H-pyrazolo[4,3-c]pyridine hydrochloride;
1-(2-aminoethyl)-3-phenyl-1H-pyrazolo[4,3-c]pyridine dihydrochloride;
1-[3-(dimethylamino)propyl]-3-phenyl-1H-pyrazolo[4,3-c]pyridine dihydrochloride;
1-[3-(dimethylamino)ethyl]-3-(4-chlorophenyl)-1H-pyrazolo[4,3-c]pyridine dimaleate;
1-[3-(methylamino)propyl]-3-(4-chlorophenyl)-1H-pyrazolo[4,3-c]pyridine dimaleate;
1-[2-(1H-imidazolyl)ethyl]-3-phenyl-1H-pyrazolo[4,3-c]pyridine;
1-(2-aminoethyl)-3-(4-pyridyl)-1H-pyrazolo[4,3-c]pyridine dimaleate;
1-(4-aminobutyl)-3-(4-pyridyl)-1H-pyrazolo[4,3-c]pyridine dimaleate;
1-(3-aminopropyl)-3-(4-pyridyl)-1H-pyrazolo[4,3-c]pyridine fumarate;
3-(3,4-dichlorophenyl)-1-(1-methyl-4-piperidinyl)-1H-pyrazolo[4,3-c]pyridine;
3-(4-trifluoromethylphenyl)-1-(1-methyl-4-piperidinyl)-1H-pyrazolo[4,3-c]pyridine sesquifumarate;
1-[3-(1-piperidinyl)propyl]-3-(4-chlorophenyl)-1H-pyrazolo[4,3-c]pyridine dimaleate;
[3-phenyl-1H-pyrazolo[4,3-c]pyridin-1-yl]acetonitrile;
3-(2-bromophenyl)-1H-pyrazolo[4,3-c]pyridine;
3-(3-bromophenyl)-1H-pyrazolo[4,3-c]pyridine;
3-(2-chlorophenyl)-1H-pyrazolo[4,3-c]pyridine maleate;
3-(4-bromophenyl)-1H-pyrazolo[4,3-c]pyridine;
1-(2-aminoethyl)-3-(2-bromophenyl)-1H-pyrazolo[4,3-c]pyridine dihydrochloride;
1-(3-aminopropyl)-3-phenyl-1H-pyrazolo[4,3-c]pyridine dihydrochloride;
1-(3-aminopropyl)-3-(2-bromophenyl)-1H-pyrazolo[4,3-c]pyridine dihydrochloride;
1-[3-aminopropyl]-3-(4-chlorophenyl)-1H-pyrazolo[4,3-c]pyridine dimaleate;
1-[2-aminoethyl]-3-(2-chlorophenyl)-1H-pyrazolo[4,3-c]pyridine sesquifumarate;
1-[3-(dimethylamino)propyl]-3-(2-bromophenyl)-1H-pyrazolo[4,3-c]pyridine dihydrochloride hemihydrate;
1-[2-(dimethylamino)ethyl]-3-(2-bromophenyl)-1H-pyrazolo[4,3-c]pyridine dihydrochloride hydrate;
1-[2-(dimethylamino)ethyl]-3-(3-bromophenyl)-1H-pyrazolo[4,3-c]pyridine dihydrochloride sesquihydrate;
1-[3-(dimethylamino)propyl]-3-(3-bromophenyl)-1H-pyrazolo[4,3-c]pyridine dihydrochloride hemihydrate;
1-[3-(dimethylamino)propyl]-3-(4-chlorophenyl)-1H-pyrazolo[4,3-c]pyridine dimaleate;
1-[2-(methylamino)ethyl]-3-(4-bromophenyl)-1H-pyrazolo[4,3-c]pyridine;
1-[2-(methylamino)ethyl]-3-(4-chlorophenyl)-1H-pyrazolo[4,3-c]pyridine sesquimaleate;
1-[3-(methylamino)propyl]-3-(4-bromophenyl)-1H-pyrazolo[4,3-c]pyridine dimaleate;
1-[3-(methylamino)propyl]-3-(2-bromophenyl)-1H-pyrazolo[4,3-c]pyridine sesquioxalate;
1-[2-(1H-imidazolyl)ethyl]-3-(4-chlorophenyl)-1H-pyrazolo[4,3-c]pyridine dimaleate;
1-[2-(1H-imidazolyl)ethyl]-3-(3,4-dichlorophenyl)-1H-pyrazolo[4,3-c]pyridine dimaleate;
1-[2-(2-methyl-1H-imidazolyl)ethyl]-3-(3,4-dichlorophenyl)-1H-pyrazolo[4,3-c]pyridine dimaleate; and
1-[2-(2-methyl-1H-imidazolyl)ethyl]-3-(4-chlorophenyl)-1H-pyrazolo[4,3-c]pyridine hemifumarate.

The following examples illustrate the preparation of some of the compounds of the invention and are not to be construed as limiting the invention disclosed herein. All temperatures are given in degrees centigrade (°C.) unless indicated otherwise.

EXAMPLE 1

3-(4-Chlorophenyl)-1H-pyrazolo-[4,3-c]pyridine hydrochloride

To a chilled (acetone/CO$_2$) solution of lithium diisopropylamide•tetrahydrofuran (THF) (200 ml) in 250 ml THF was added a solution of 4-chloropyridine in 35 ml THF. After stirring for 4 hours, a solution of 4-chlorobenzaldehyde in 60 ml THF was added. The solution was allowed to come to room temperature, then worked up with water and extracted twice with ethyl acetate. The combined organics were washed with water and dried (saturated NaCl solution, MgSO$_4$). The solvents were concentrated and the resulting solid was triturated with ethyl ether to give 41.3 g of a solid.

A suspension of the alcohol (9.5 g) from the previous step and manganese (IV) oxide (6.5 g) in 150 ml toluene was refluxed for 1.5 hours. Filtration through celite and concentration of the solvents gave 9.1 g of the ketone as an oil.

A solution of the ketone (9.1 g) in 50 ml ethanol was treated with 4.4 ml of hydrazine hydrate. After refluxing for 2 hours, the mixture was poured into iced water and the resulting solid was filtered and rinsed with water and ether to give 6.57 g of a solid. A 3.0 g portion was recrystallized from methanol to give 2.0 g of a solid which was suspended in methanol, treated with an ethereal HCl solution and filtered. The salt was crystallized out with additional ether to give 1.95 g of a powder, m.p. 265° C. (dec).

Analysis: Calculated for C$_{12}$H$_8$ClN$_3$•HCl: 54.16%C; 3.41%H; 15.79%N; Found: 53.98%C; 3.41%H; 15.67%N.

Following a procedure similar to that described in Example 1, the following 3-(halophenyl)-1H-pyrazolo[4,3-c]pyridines are prepared.

| Example | X | Y | Salt | m.p. (°C.)/ Recryst. Solv. |
|---------|------|---|---------|-----------|
| 1A | 2-Br | H |  | 215.5-216.5 diethyl ether |
| 1B | 3-Br | H | — | >250 water wash |
| 1C | 2-Cl | H | maleate | 175-177 methanol-ether |
| 1D | 4-Br | H | — | >250 water wash |

EXAMPLE 2

1-(2-Aminoethyl)-3-phenyl-1H-pyrazolo-[4,3-c]pyridine dihydrochloride

3-Phenyl-1H-pyrazolo[4,3-c]pyridine (1.95 g) was suspended in 50 ml of dimethylformamide to which 2-bromoethylphthalimide (2.54) and K$_2$CO$_3$ (1.4 g) had been added. This mixture was stirred and warmed at 90° C. for 4 hours and then an additional 1.25 g of 2-bromoethylphthalimide and 0.7 g of K$_2$CO$_3$ were added. After 2 more hours another 0.60 g of 2-bromoethylphthalimide and 0.4 g of K$_2$CO$_3$ were added and stirring and heating were continued for an additional 90 minutes. At the end of this time, the reaction mixture was poured into H$_2$O and the product filtered off and dried to give 2.63 of 3-phenyl-1-[2-(phthalimido)ethyl]-1H-pyrazolo[4,3-c]pyridine.

The phthalimide prepared above (4.60 g) was warmed at 55° C. in 20 ml of hydrazine hydrate for 1 hour. At the end of this time the mixture was distributed between H$_2$O and ethyl acetate and the organic phase was separated. The aqueous phase was extracted twice more with ethyl acetate and the combined organic phase was dried and evaporated. The dihydrochloride was formed in methanol and recrystallized from methanol-diethyl ether to give 2.10 g, m.p. 295° (dec).

Analysis: Calculated for C$_{14}$H$_{14}$N$_4$•2HCl: 54.03%C; 5.18%H; 18.00%N; Found: 53.76%C; 5.20%H; 17.70%N.

Following a procedure similar to that described in Example 2 above, using an appropriate bromoalkylphthalimide, the following 1-(2-aminoalkyl)-3-(phenyl or substituted phenyl)-1H-pyrazolo[4,3-c]pyridines are prepared.

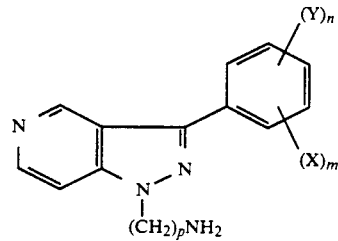

| Example | X | Y | p | Salt | m.p. (°C.)/ Recryst. Solv. |
|---------|------|------|---|------|-----------|
| 2A | 2-Br | H | 2 | di-HCl | 250 (dec) methanol |
| 2B | H | H | 3 | di-HCl | 260 (dec) methanol |
| 2C | 2-Br | H | 3 | di-HCl | >250 methanol |
| 2D | 4-Cl | H | 3 | dimaleate | 146-149 (dec)/ methanol-ether |
| 2E | 2-Cl | H | 2 | sesqui-fumarate | 197-198 (dec)/ methanol |
| 2F | 4-Cl | H | 2 | dimaleate | 150-152 (dec)/ methanol-ether |
| 2F | 3-Br | H | 2 | di-HCl | 235/ methanol-ether |
| 2G | 3-Br | H | 3 | di-HCl hemihydrate | >250/methanol |
| 2H | 4-Br | H | 2 | — | 107.5-109/ ether |
| 2I | 4-Br | H | 3 | diHCl | >250/ methanol-ether |
| 2J | 2-Cl | H | 3 | fumarate | 150-153 (dec)/ methanol-ether |
| 2K | 3-Cl | 4-Cl | 3 | maleate | 191 (dec)/ methanol-ether |
| 2L | 3-Cl | 4-Cl | 2 | maleate | 200 (dec)/ methanol |
| 2M | 3-Cl | 4-Cl | 4 | maleate | 172.5 (dec)/ methanol-ether |
| 2N | 4-Cl | H | 4 | dimaleate | 143-144 (dec)/ methanol-ether |
| 2P | 4-CF$_3$ | H | 4 | maleate | 171 (dec)/ methanol-ether |
| 2Q | 4-CF$_3$ | H | 2 | maleate | 180 (dec)/ methanol |
| 2R | 4-CF$_3$ | H | 3 | maleate | 174 (dec)/ methanol-ether |
| 2S | 2-Cl | 4-Cl | 2 | fumarate | 246 (dec)/ methanol |
| 2T | 2-CH$_3$ | H | 2 | sesqui-fumarate | 195-195.5 (dec)/ methanol |
| 2U | 2-CH$_3$ | H | 3 | sesqui-fumarate hemihydrate | 174-175/ methanol |
| 2V | 2-Cl | 4-Cl | 3 | dimaleate | 75-77/ |

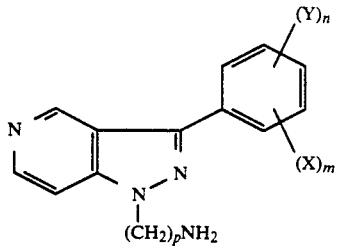

| Example | X | Y | p | Salt | m.p. (°C.)/ Recryst. Solv. |
|---|---|---|---|---|---|
| 2W | 2-F | H | 3 | hemihydrate dimaleate | 152–153.5/ methanol |
| 2X | 2-F | H | 2 | fumarate | 167.5 (dec)/ methanol-ether |
| 2Y | 2-Cl | 6-Cl | 2 | fumarate | 195–196/ methanol |
| 2Z | 4-NO₂ | H | 2 | hemi-fumarate | 233 (dec)/ methanol |
| 2AA | 4-NO₂ | H | 3 | fumarate | 213 (dec)/ methanol |
| 2BB | 2-Cl | 6-Cl | 3 | fumarate | 183–184/ methanol |
| 2CC | 2-Cl | 3-Cl | 2 | fumarate | 217 (dec)/ methanol-ether |
| 2DD | 2-Cl | 3-Cl | 3 | fumarate | 170 (dec)/ methanol |
| 2EE | 2-Cl, 3-Cl | 4-Cl | 2 | fumarate | 250 (dec)/ methanol |
| 2FF | 2-Cl, 3-Cl | 4-Cl | 3 | fumarate | 208 (dec)/ methanol |
| 2GG | 2-OCH₃ | H | 3 | dimaleate | 149–150/ methanol, ethyl acetate |
| 2HH | 2-OCH₃ | H | 2 | dimaleate | 173–174 (dec)/ methanol |

EXAMPLE 3

1-[3-(Dimethylamino)propyl]-3-phenyl-1H-pyrazolo-[4,3-c]pyridine dihydrochloride 3-Phenyl-1H-pyrazolo[4,3-c]pyridine (3.90 g) was suspended in 50 ml of dimethylformamide and 60% NaH (1.0 g) was added. After stirring for 90 minutes, dimethylaminopropyl chloride (3.0 g) was added, and stirring was continued for 1 hour. At the end of this time the reaction was warmed to 55° and, after an additional 2 hours, an additional 0.50 g of dimethylaminopropyl chloride was added. Warming and stirring was continued for 1 hour, after which time the reaction mixture was distributed between ether and H₂O. The organic phase was dried, evaporated, and purified by flash chromatography (5% triethylamine-ethyl acetate), giving an oil upon evaporation of the product-containing fractions. The hydrochloride was formed in ethereal HCl and recrystallized from methanol-ether to give 3.76 g of product, m.p. 237°–239°.

Analysis: Calculated for C₁₇H₂₀N₄•2HCl: 57.80%C; 6.28%H; 15.86%N; Found: 57.76%C; 6.53%H; 15.70%N.

EXAMPLE 4

1-[2-(Dimethylamino)ethyl]-3-(4-chlorophenyl)-1H-pyrazolo[4,3-c]-pyridine dimaleate A mixture of 3-(4-chlorophenyl)-1H-pyrazolo[4,3-c]pyridine (3.47 g), potassium carbonate (2.4 g) and dimethylaminoethyl chloride hydrochloride (4.6 g) in 50 ml DMF was heated at 85° C. for 1 hour. The reaction was quenched into iced water and extracted three times with ethyl acetate. The combined organics were washed with water and dried (saturated NaCl, MgSO₄). The compound was purified via flash chromatography (5→10% triethylamine/ethyl acetate) to give 3.47 g of an oil. The oil was dissolved in methanol, treated with 2.1 equivalents of maleic acid and crystallized with ethyl ether to give 4.95 g of a powder, m.p. 134°–136° C.

Analysis: Calculated for C₁₆H₁₇ClN₄•2C₄H₄O₄: 54.09%C; 4.73%H; 10.51%N; Found: 54.07%C; 4.69%H; 10.45%N.

Following a procedure similar to that described in Example 4, using an appropriate dimethylaminoalkyl-chloride, the following 1-[ω-(dimethylamino)alkyl]-3-(phenyl or substituted phenyl)-1H-pyrazolo[4,3-c]pyridines are prepared.

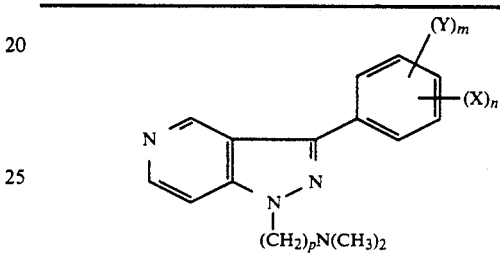

| Example | X | Y | P | Salt/ Hydrate | m.p. (°C.)/ Recryst. Solv. |
|---|---|---|---|---|---|
| 4A | 2-Br | H | 3 | di-HCl/ hemihydrate | 120/methanol-ethyl acetate |
| 4B | 2-Br | H | 2 | di-HCl/ hydrate | 207/methanol-ether |
| 4C | 3-Br | H | 2 | di-HCl/ 1.5 Hydrate | 134–136/ methanol-ether |
| 4D | 3-Br | H | 3 | di-HCl/ hemi-hydrate | 138–140/ methanol-ether |
| 4E | 4-Cl | H | 3 | dimaleate | 129–131 (dec)/ methanol-ether |
| 4F | H | H | 2 | dimaleate | 134–135/ methanol-ether |
| 4G | 4-Br | H | 3 | dimaleate | 129–130/ methanol-ether |
| 4H | 4-Br | H | 2 | dimaleate | 139–140/ methanol-ether |
| 4I | 2-Cl | H | 3 | fumarate | 156–158 (dec) methanol-ether |
| 4J | 2-Cl | H | 2 | di-HCl/ .25 hydrate | 205–207/methanol-ethyl acetate |

EXAMPLE 5

1-[3-Methylaminopropyl]-3-(4-chlorophenyl)-1H-pyrazolo-[4,3-c]-pyridine dimaleate A mixture of 1-[3-aminopropyl]-3-(4-chlorophenyl)-1H-pyrazolo[4,3-c]pyridine dimaleate (3.3 g), methyl trifluoroacetate (1.27 ml) and triethylamine (1.9 ml) in 75 ml methanol was stirred at ambient temperature for 45 minutes. Concentration of the mixture and trituration of the resulting solid with ether gave 3.76 g of a powder, m.p. 122°–125° C.

A mixture of the trifluoroacetamide (3.19 g) and potassium t-butoxide (1.07 g) in 70 ml THF was treated with dimethyl sulfate (0.83 ml). After stirring at ambient temperature for 1 hour the reaction was quenched with aqueous ammonia and the aqueous was extracted three times with ethyl acetate. The combined organics were washed with water and dried (saturated NaCl, MgSO₄).

Concentration of the solvent gave 3.6 g of a solid which was used in the next step.

The methyl derivative was stirred for 45 minutes in a mixture of 50 ml methanol and 50 ml saturated potassium carbonate solution. The mixture was partitioned between ethyl acetate and water and the aqueous was extracted twice with ethyl acetate. The combined organics were dried with MgSO$_4$. The desired compound was purified via flash chromatography (dichloromethane, methanol, triethylamine; 18:1:1) to give 1.11 g of an oil. This oil was dissolved in methanol treated with 2.1 equivalents of maleic acid and crystallized with ethyl ether to give 0.979 g of a powder, m.p. 149°–150° C.

Analysis: Calculated for $C_{16}H_{17}ClN_4 \cdot 2C_4H_4O_4$: 54.09%C; 4.73%H; 10.51%N; Found: 53.70%C; 4.44%H; 10.42%N.

Following a procedure similar to that described in Example 5, using an appropriate starting primary amine, the following 1-[methylaminoalkyl]-3-[substituted phenyl]-1H-pyrazolo[4,3-c]pyridines are prepared.

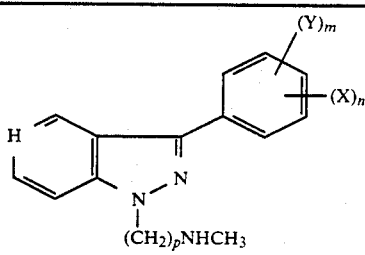

| Starting Amine | Ex. # | X | Y | P | Salt/ Hydrate | m.p. (°C.)/ Recryst. Solv. |
|---|---|---|---|---|---|---|
| Ex. 2H | 5A | 4-Br | H | 2 | — | 60–61/ ether-pentane |
| Ex. 2F | 5B | 4-Cl | H | 2 | 1.5 maleate | 169–170 (dec)/ methanol-ether |
| Ex. 2I | 5C | 4-Br | H | 3 | dimaleate | 153–154/ methanol-ether |
| Ex. 2C | 5D | 2-Br | H | 3 | 1.5 oxalate | 117 (dec)/ methanol-ether |
| Ex. 2A | 5E | 2-Br | H | 2 | 1.5 fumarate | 170–172/ methanol-ether |
| Ex. 2F | 5F | 3-Br | H | 2 | — | 71–72.5/ether |

EXAMPLE 6

1-[2-(1H-Imidazoyl)ethyl]-3-phenyl-1H-pyrazolo[4,3-c]pyridine

3-Phenyl-1H-pyrazolo[4,3-c]pyridine (2.93 g) was suspended in 30 ml of N,N-dimethylformamide to which 1-(2-chloroethyl)imidazole (2.15 g) and K$_2$CO$_3$ (2.3 g) had been added. This mixture was stirred and warmed at 90° for 2 hours and then an additional 0.20 g of 1-(2-chloroethyl)imidazole and 0.2 g of K$_2$CO$_3$ were added. After an additional 45 minutes, the reaction mixture was distributed between H$_2$O and ethyl acetate and the organic phase was washed with water. Evaporation and trituration with ether gave 2.15 g of product after recrystallization from CH$_2$Cl$_2$-pentane, mp 123°–125°.

Analysis: Calculated for $C_{17}H_{15}N_5$: 70.57%C; 5.23%H; 24.20%N; Found: 70.45%C; 5.24%H; 24.18%N.

Following a procedure similar to that described in Example 6, using an appropriate 3-(4-phenyl or substituted phenyl)-1H-pyrazolo[4.3-c]piperidine, the following 1-[2-(1H-imidazolyl or methyl-1H-imidazolyl)alkyl]-3-(phenyl or substituted phenyl)-1H-pyrazolo[4,3-c]piperidines are prepared.

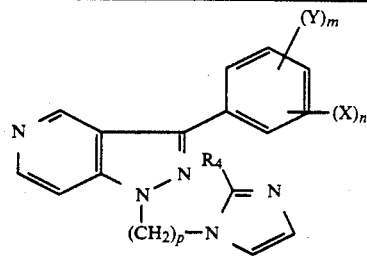

| EX. | X | Y | R$_4$ | q | Salt/ Hydrate | m.p./ Recryst. Solvent |
|---|---|---|---|---|---|---|
| 6A | 4-Cl | H | H | 2 | dimaleate | 155–156 (dec)/ methanol-ether |
| 6B | 3-Cl | 4-Cl | H | 2 | dimaleate | 140.5–141.5/ methanol-ether |
| 6C | 3-Cl | 4-Cl | CH$_3$ | 2 | dimaleate | 146–148/ methanol-ether |
| 6D | 4-Cl | H | CH$_3$ | 2 | hemifumarate | 215–217 (dec)/ methanol-ether |
| 6E | H | H | CH$_3$ | 2 | di-HCl/.25 hydrate | 233–235/ methanol-ether |

EXAMPLE 7

1-(2-Aminoethyl)-3-(4-pyridyl)-1H-pyrazolo[4,3-c]-pyridine dimaleate

A mixture of 3-(4-pyridyl)-1H-pyrazolo[4,3-c]pyridine (3.0 g), potassium carbonate (3.17 g) and N-(2-Bromoethyl)-phthalimide (5.84) in DMF (70 ml) was heated at 90° C. for one hour. The reaction was cooled, diluted with water and extracted with dichloromethane. The organics were washed with water, dried (MgSO$_4$), and filtered over a column of florisil eluting the product with ethyl acetate, then 5% triethylamine/ethyl acetate. Concentration followed by trituration with diethyl ether yielded 4.56 g of the phthalimide derivative.

The derivative was boiled for 2.5 hours in ethanol (250 ml) containing hydrazine monohydrate (4.0 ml). The reaction was cooled, diluted with water and extracted with dichloromethane. The organics were washed with water and brine, dried (MgSO$_4$), concentrated, and triturated with diethyl ether to yield 0.941 mg of product. The dimaleate was formed from methanol/diethyl ether, filtered, washed with diethyl ether, and dried under high vacuum and refluxing isopropanol for 4.0 hours to yield 1.32 g of a solid, m.p. 149.5° C.(dec.).

Analysis: Calculated for $C_{13}H_{13}N_5 \cdot C_8H_8O_8$: 53.50%C; 4.49%H; 14.86%N; Found: 53.21%C; 4.43%H; 14.81%N.

EXAMPLE 8

1-(4-Aminobutyl)-3-(4-pyridyl)-1H-pyrazolo-[4,3-c]-pyridine dimaleate

A mixture of 3-(4-pyridyl)-1H-pyrazolo[4,3-c]pyridine (4.0 g), potassium carbonate (2.96 g) and N-(4-bromobutyl)-phthalimide (6.05 g) in DMF (90 ml) was heated at 90° for one hour. An additional 150 mg of potassium carbonate and 300 mg of the phthalimide was added and heating was continued for two hours. The reaction was cooled, diluted with water and extracted with ethyl acetate. The organics were washed with water, dried (MgSO$_4$), concentrated, and triturated with diethyl ether to yield 6.08 g of the phthalimide derivative.

The derivative was boiled in ethanol (200 ml) containing hydrazine monohydrate (4.0 ml) for 2.5 hours and solvent was removed by distillation. The residue was diluted with water (150 ml) and extracted with methylene chloride. The organics were washed with brine, dried (MgSO$_4$), and concentrated. The residue was adhered to florisil with methanol and flash chromatographed (florisil; 1:1:18 methanol/triethylamine/dichloromethane. The dimaleate was formed from methanol/diethyl ether, filtered, washed with diethyl ether, and dried under high vacuum and refluxing isopropanol for 4.0 hours to yield 2.15 g of a solid, m.p. 141° C.(dec.).

Analysis: Calculated for C$_{15}$H$_{17}$N$_5$•C$_8$H$_8$O$_8$: 55.31%C; 5.05%H; 14.02%N; Found: 55.09%C; 5.07%H; 14.17%N.

EXAMPLE 9

1-(3-Aminopropyl)-3-(4-pyridyl)-1H-pyrazolo[4,3-c]-pyridine fumarate

A mixture of 3-(4-pyridyl)-1H-pyrazolo[4,3-c]pyridine (3.20 g), potassium carbonate (2.37 g) and N-(3-bromopropyl)-phthalimide (4.6 g) in DMF (72 ml) was heated at 90° C. for one hour. The reaction was cooled, diluted with water and extracted with ethyl acetate. The organics were washed with water, dried (MgSO$_4$), and filtered over a column of florisil eluting first with ethyl acetate and then 5% triethylamine/ethyl acetate. Trituration with diethyl ethyl yielded 5.17 g of the phthalimide derivative.

The derivative was boiled in ethanol (200 ml) containing hydrazine monohydrate (4.0 ml) for one hour and solvent was removed by distillation. The residue was adhered to florisil with methanol and flash chromatographed (florisil; 1:1:18 triethylamine/methanol/dichloromethane) to yield 3.57 g of crude product. A portion of this product (1.77 g) was taken up in methanol and the fumarate salt was formed. The salt was recrystallized (methanol, diethyl ether and H$_2$O) and dried under high vacuum and refluxing xylenes overnight to yield 1.65 g of a solid, m.p. 200° C.(dec.).

Analysis: Calculated for C$_{14}$H$_{15}$N$_5$•C$_4$H$_4$O$_4$: 58.53%C; 5.18%H; 18.96%N; Found: 58.43%C; 5.11%H; 18.68%N.

EXAMPLE 10

3-(3,4-Dichlorophenyl)-1-(1-methyl-4-piperidinyl)-1H-pyrazolo[4,3-c]pyridine

4-Chloro-3-(3,4-dichlorobenzoyl)pyridine (2.26 g), 1-methylpiperidine-4-hydrazine (1.0 g) and titanium isopropoxide (2.27 g) were stirred together overnight in 20 ml of dichloromethane. At the end of this time, thin layer chromatography showed some starting material remaining, so an additional 1.0 g of 1-methylpiperidine-4-hydrazine and 2.27 of titanium isopropoxide were added and the reaction mixture was stirred an additional 24 hours. The reaction volume was diluted to 200 ml with dichloromethane and 5 ml of H$_2$O was added. This mixture was stirred for 15 minutes and the precipitated salts were filtered off. The filtrate was washed with water, dried, and evaporated to give 3.0 g of a solid whose $^1$H NMR was consistent with 4-chloro-3-(3,4-dichlorobenzoyl)pyridine 1-methyl-4-piperidinylhydrazone.

The hydrazone prepared in this manner was dissolved in 25 ml of tetrahydrofuran and treated with 0.90 g of potassium t-butoxide. After 30 minutes, the reaction mixture was distributed between H$_2$O and ethyl acetate and the organic phase was dried and evaporated. The residue obtained was triturated with ether to give 1.43 g of product. The filtrate was evaporated and further purified by flash chromatography (18:1:1, ethyl acetate:methanol:triethylamine) to yield an additional 0.40 g of product. The combined product was recrystallized from MeOH-H$_2$O to give 1.50 g, m.p.: 179°-180° C.(dec.).

Analysis: Calculated for C$_{18}$H$_{18}$Cl$_2$N$_4$: 59.84%C; 5.02%H; 15.51%N; Found: 59.83%C; 4.90%H; 15.47%N.

EXAMPLE 11

3-(4-Trifluoromethylphenyl)-1-(1-methyl-4-piperidinyl)-1H-pyrazolo-[4,3-c]pyridine sesquifumarate 4-Chloro-3-(4-trifluoromethylbenzoyl)pyridine (2.28 g), 1-methylpiperidine-4-hydrazine (1.5 g) and titanium isopropoxide (3.3 g) were stirred together overnight in 20 ml of dichloromethane. At the end of this time, thin layer chromatography showed some starting material remaining, so an additional 0.5 g of 1-methylpiperidine-4-hydrazine and 1.1 g of titanium isopropoxide were added and the reaction mixture stirred an additional 24 hours. The reaction volume was diluted to 200 ml with dichloromethane and then 5 ml of H$_2$O was added. This mixture was stirred for 15 minutes, and then the precipitated salts were filtered off. The filtrate was washed with water, dried, and evaporated to give 2.96 of a solid whose $^1$H NMR was consistent with 4-chloro-3-(4-rifluoromethylbenzoyl)pyridine-1-methyl-4-piperidinylhydrazone.

The hydrazone prepared in this manner was dissolved in 50 ml of THF and treated with 0.90 g of potassium t-butoxide. After 30 minutes, the reaction mixture was distributed between H$_2$O and ethyl acetate and then the organic phase was dried and evaporated. The residue obtained was purified by flash chromatography (18:1:1, ethyl acetate:methanol:triethylamine) to yield 1.61 g of product as an oil. The oil was taken up in 20 ml of acetone to which 2.1 g of fumaric acid was then added. The product was filtered off and recrystallized from acetonitrile-H$_2$O to give 1.21 g of the sesquifumarate, m.p.: 240° C.(dec.).

Analysis: Calculated for C$_{19}$H$_{19}$F$_3$N$_4$•1.5C$_4$H$_4$O$_4$: 56.18%C; 4.71%H; 10.48%N; Found: 55.99%C; 4.61%H; 10.38%N.

EXAMPLE 12

1-[3-(1-Piperidinyl)propyl]-3-(4-chlorophenyl)-1H-pyrazolo[4,3-c]pyridine dimaleate A mixture of 3-(4-chlorophenyl)-1H-pyrazolo[4,3-c]pyridine (2.57 g), potassium carbonate (3.3 g) and 3-chloropropyl piperidine hydrochloride (2.44 g) in 45 ml dimethylformamide was heated at 85° C. for 2 hours. The reaction was quenched into iced water and extracted three times with ethyl acetate. The combined organics were washed with water and dried (saturated NaCl, MgSO$_4$). The compound was purified via flash chromatography (2→4% triethylamine/ethyl acetate) to give 3.6 g of an oil. This was dissolved in methanol, treated with 2.1 equivalents of maleic acid and the salt was crystallized out with ethyl ether to give 5.22 g of a powder, m.p. 160°–162° C.

Analysis: Calculated for $C_{20}H_{23}ClN_4 \cdot 2C_4H_4O_4$: 57.29%C; 5.32%H; 9.54%N; Found: 57.33%C; 5.30%H; 9.50%N.

EXAMPLE 13

[3-Phenyl-1H-pyrazolo[4,3-c]pyridin-1-yl]acetonitrile

3-Phenyl-1H-pyrazolo[4,3-c]pyridine (5.85 g) was suspended in 75 ml of DMF and 60% NaH (1.5 g) was added. After stirring for 90 minutes, chloroacetonitrile (2.64 g) was added, and stirring was continued for 1 hour. At the end of this time, an additional 1.00 g of chloroacetonirile was added and stirring was continued for 1 hour. The reaction mixture was then poured into $H_2O$ and the crude product was filtered off and purified by flash chromatography (50% ethyl acetate/DCM). Evaporation of the product-containing fractions gave 4.90 g of product. Analytically pure material was obtained by recrystallization from ethyl acetate-pentane, m.p. 148°–149°.

Analysis: Calculated for $C_{14}H_{10}N_4$: 71.78%C; 4.30%H; 23.92%N; Found: 71.96%C; 4.18%H; 23.97%N.

We claim:

1. A compound of the formula

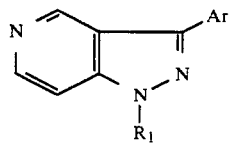

wherein
Ar is

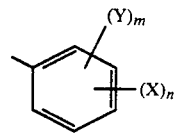

or pyridyl;
$R_1$ is hydrogen;
X and Y are independently hydrogen, halogen, trifluoromethyl, loweralkyl, loweralkoxy, nitro or hydroxy;
with the proviso that X and Y cannot both be hydrogen;
n is 1, 2 or 3;
m is 1 or 2;
or a pharmaceutically acceptable addition salt and/or hydrate thereof, or where applicable, the optical or geometric isomer or racemic mixture thereof.

2. The compound as defined in claim 1 wherein Ar is

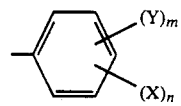

and $R_1$ is hydrogen.

3. A compound as defined in claim 2 which is 3-(4-chlorophenyl)-1H-pyrazolo[4,3-c]-pyridine.

4. A compound as defined in claim 2 which is 3-(2-bromophenyl)-1H-pyrazolo[4,3-c]pyridine.

5. A compound as defined in claim 2 which is 3-(3-bromophenyl)-1H-pyrazolo[4,3-c]pyridine.

6. A compound as defined in claim 2 which is 3-(2-chlorophenyl)-1H pyrazolo[4,3-c]pyridine.

7. A compound as defined in claim 2 which is 3-(4-bromophenyl)-1H pyrazolo[4,3-c]pyridine.

* * * * *